US007871386B2

(12) United States Patent
Nan

(10) Patent No.: US 7,871,386 B2
(45) Date of Patent: Jan. 18, 2011

(54) MINIATURE MASSAGE VIBRATOR

(75) Inventor: Simon Siu Man Nan, Richmond Hill (CA)

(73) Assignee: Nanma Manufacturing Co., Ltd. (HK)

( * ) Notice: Subject to any disclaimer, the term of this patent is extended or adjusted under 35 U.S.C. 154(b) by 977 days.

(21) Appl. No.: 11/724,819

(22) Filed: Mar. 16, 2007

(65) Prior Publication Data

US 2008/0228114 A1 Sep. 18, 2008

(51) Int. Cl.
*A61H 1/00* (2006.01)
*A61F 5/00* (2006.01)

(52) U.S. Cl. .............................. 601/46; 601/70; 600/38

(58) Field of Classification Search ................... 601/46, 601/67, 69, 70, 72, 80; 600/38
See application file for complete search history.

(56) References Cited

U.S. PATENT DOCUMENTS

| | | | | |
|---|---|---|---|---|
| 3,451,391 | A * | 6/1969 | Tavel | 601/72 |
| 6,432,071 | B1 * | 8/2002 | Hsieh | 601/72 |
| 2003/0181835 | A1 * | 9/2003 | Klein | 601/72 |

* cited by examiner

*Primary Examiner*—Quang D Thanh
(74) *Attorney, Agent, or Firm*—Polsinelli Shughart PC

(57) ABSTRACT

A miniature electrically powered massage vibrator includes an outermost shell slideably holding a vibrating body, i.e., a vibration generator. The vibrating body contains a power source of button-type battery cells for powering a motor of the vibration generator encased inside the body, and a power switching mechanism. Sliding movement of the outermost shell relative to the vibrating body provides the switching on/off functions of the electric power. The massage vibrator is useful for sexual assistance or marital aid or therapeutic use.

8 Claims, 5 Drawing Sheets

MINIATURE MASSAGE VIBRATOR

BACKGROUND

The present invention relates generally to sexual assistance or marital aid or therapeutic devices, and particularly to a miniature electrically powered massage vibrator encased in a resilient housing worn by a user for transferring vibration to a partner of the user.

Prior art miniature sexual aid or stimulating devices with a miniaturized massage vibrator generally have a mechanical switch which is manually actuated for the On/Off operation of the vibrator.

Existing designs of the switch face a problem that the On/Off switch is too small to easily operate. However, on the other hand the switch cannot be made in a larger size as this could affect the normal application and use of the vibrator.

Another problem faced by existing designs is the orientation of the switching direction relative to the device body. For example, in current vibrator devices, the switch is frequently positioned so as to be mistakenly actuated (switched off) by the motions of the massage action.

Another problem of existing designs relates to the availability or inclusion of a battery carrying means or device. That is, some vibrators do not have capability for battery changes. Certain other vibrators do not have a secure battery cover.

The present invention was therefore developed to provide for a miniature, electrically powered massage vibrator that overcomes one or more shortcomings of existing vibrator devices.

BRIEF SUMMARY OF THE INVENTION

A device of the present character is intended for transferring vibration to the female clitoris during intercourse. For example, embodiments of the presently described technology provide a miniature electrically powered massage vibrator that is encased in resilient housing and can be worn on the base of the penis for such purposes.

Among the advantages, benefits, features, goals and objectives relative to one or more embodiments of the present invention include the provision of a miniature ("mini") electrically powered massage vibrator device (thus referred to as a "mini vibrator") which of extreme compactness and miniature nature, which is capable of being worn on the male sex organ for stimulating the female clitoris during the act of sexual intercourse, as a sexual aid or for therapeutic purposes, for example. One or more embodiments of the device have a reduced overall dimension that can be effectively disposed at and provide vibrations to the sexual regions of partners. One or more embodiments of the device includes an effective on/off switch arrangement that, despite the miniaturized, very compact nature of the new device, is ergonomically convenient for operation of the device and is more difficult to be mistakenly actuated by movements of and/or use of the device during movements such as a massage action. One or more embodiments of the device includes an effective arrangement and means for changing one or more batteries of the device and which provides a more secure battery cover.

Briefly, according to one or more embodiments of the present invention there is provided a miniature electrically powered massage vibrator with an outermost shell slideably holding a vibrating body, that is, a vibration generator. The vibrating body includes a power source (of button-type battery cells, for example) for powering a motor of the vibration generator that is encased inside the body. The vibrating body also includes a power switching mechanism.

A sliding movement of the outermost shell relative to the vibrating body can provide the switching on/off functions of the electric power to the device. In a preferred application, this miniature vibrator can be encased in a soft resilient casing which is worn by a male user on the base of his sexual organ for providing stimulation to the organ of sexual partner of the user during intercourse.

DRAWINGS

Corresponding reference characters indicate corresponding parts in multiple figures of the drawings.

Figure 1:
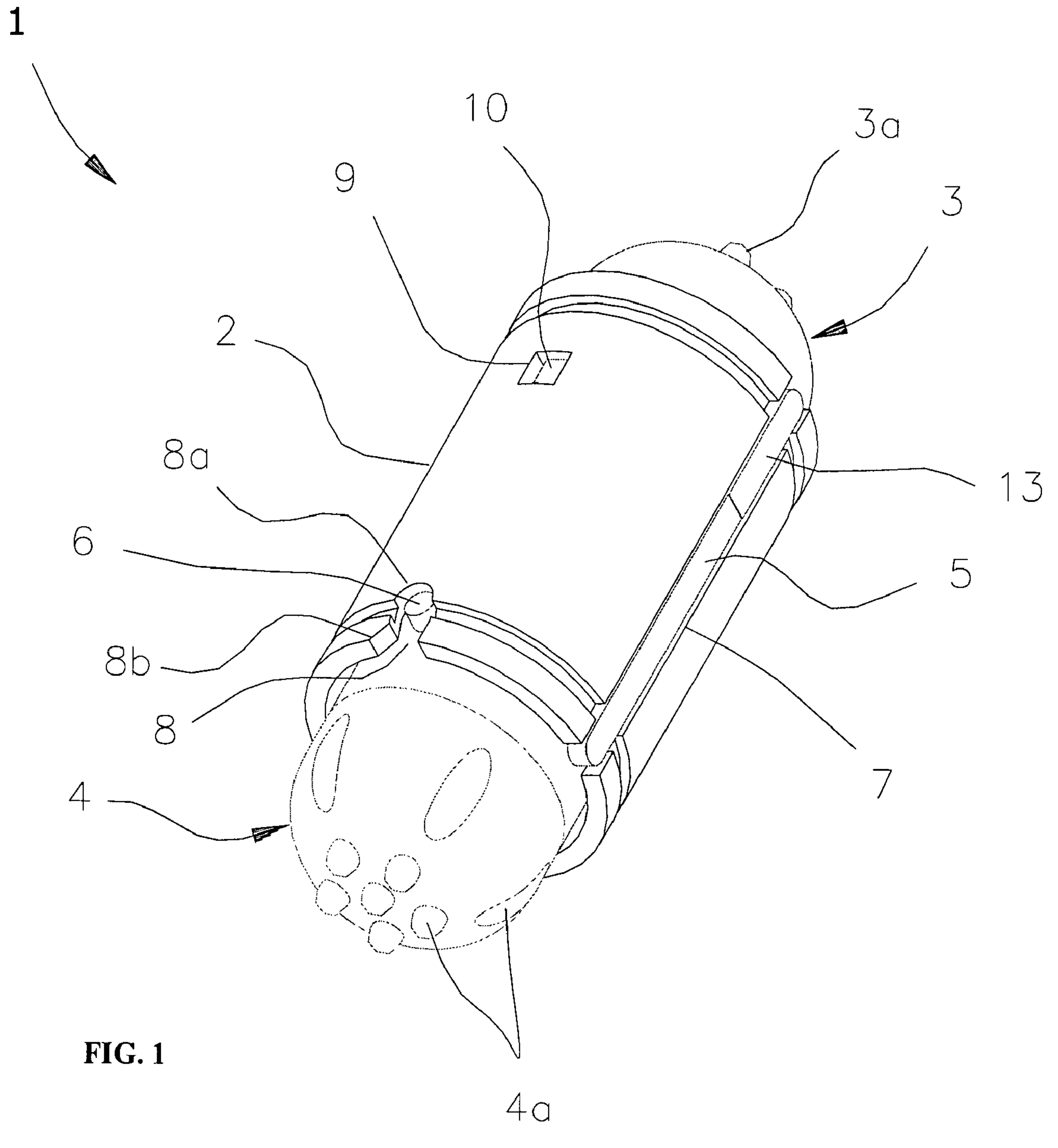
FIG. 1 illustrates a perspective-type view of the massage device in accordance with an embodiment of the presently described invention.

The foregoing summary, as well as the following detailed description of certain embodiments of the presently described technology, will be better understood when read in conjunction with the appended drawings. For the purpose of illustrating the presently described technology, certain embodiments are shown in the drawings. It should be understood, however, that the presently described technology is not limited to the arrangements and instrumentality shown in the attached drawings.

DESCRIPTION

A preferred embodiment of an embodiment of the presently described invention is presented, by way of example only, with reference to the accompanying drawings.

Referring to FIG. 1, in one preferred embodiment of the present invention, powered miniature vibrator 1 comprises an outermost shell 2 slideably holding a vibrating body 3 with a battery cover unit 4 containing an electric motor, a battery chamber carrying button cell-type batteries and a power switching mechanism Outmost shell 2 is a cylindrical hollow tube having a longitudinal slot 7 which is slideably engaged to key portions 5 and 13 on the surface of vibration body 3. The engagement of slot 7 and such key portions provides a sliding guide for a longitudinal relative movement between outermost shell 2 and vibrating body 3, and it also introduces a restriction of inhibiting and even preventing the rotational relative movement between the outmost shell and the vibrating body.

Cylindrical block 6 protrudes outwardly from the surface of vibrating body 3. At a proximal end of outermost shell 2 there is a short curved slot 8 having two ends 8*a* and 8*b*. Cylindrical block 6 is engaged with the slot 8. When outermost shell 2 is made to move relative to vibrating body 3, block 6 has to overcome a larger friction at the middle portion of slot 8 due to its curved shape and the restriction of rotational relative movement between the outmost shell and the vibrating body, so that block 6 tends to stay at either end 8*a* or end 8*b* of the slot.

At the distal end of outermost shell 2 one or more holes 9 are disposed. For example, in an embodiment, two holes 9 of rectangular shape are disposed circumferentially at 180° apart. Each one of holes 9 is engaged with an arm 10 of a switch ring encased in the vibrating body 3. Start/stop positions of block 6 at 8*a* and 8*b* in the slot respectively define on and off positions of the power switching system or arrangement. That is, block 6 can be moved between being at 8*a* and being at 8*b*. In an embodiment, when block 6 is at 8*a*, the power switching system can be on and when block 6 is at 8*b*, the system can be off (and vice-versa).

Figure 2:
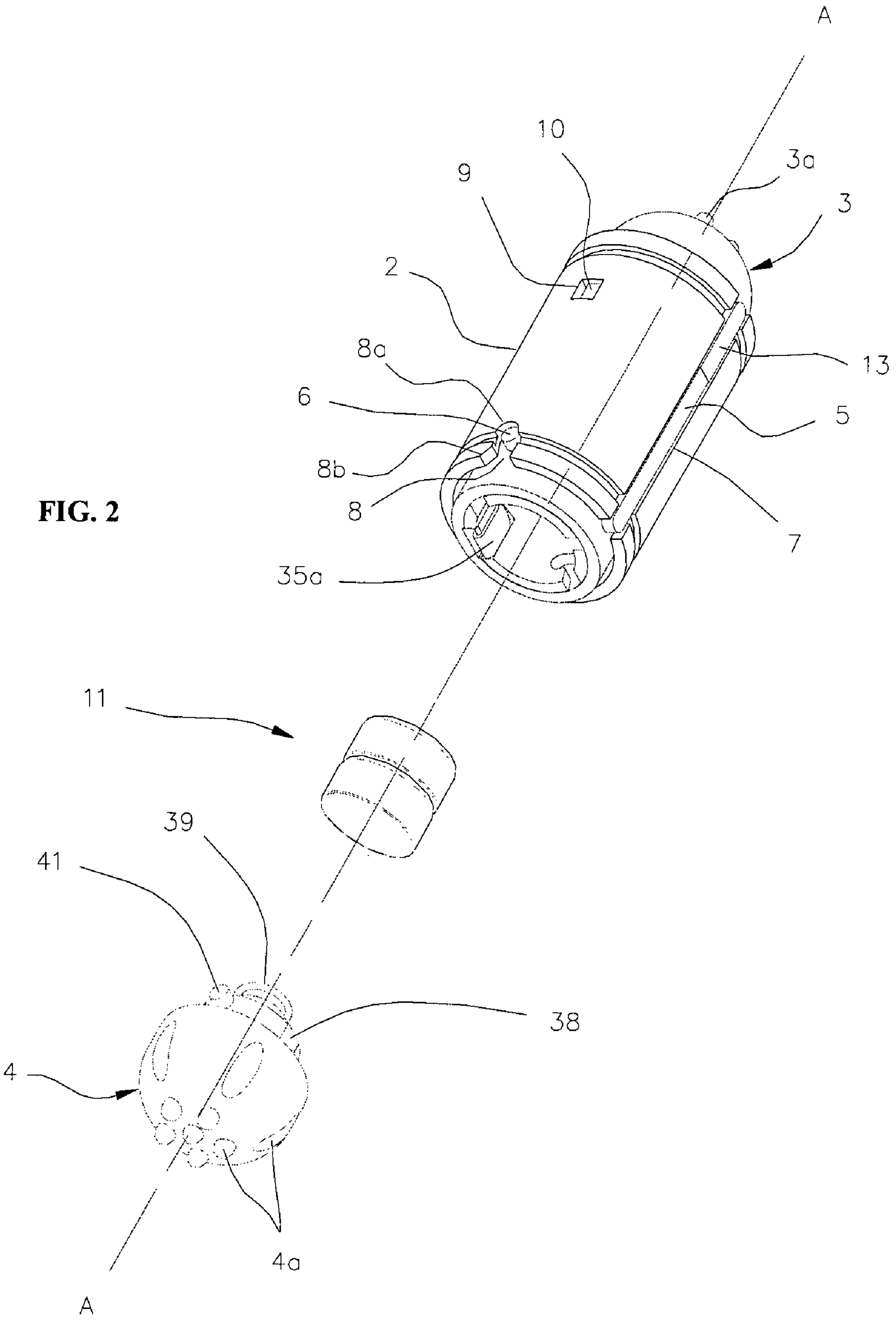
FIG. 2 illustrates a perspective-type view of the massage device shown in FIG. 1 with the battery cover and batteries detached from the vibration body in accordance with an embodiment of the presently described invention.

Referring to FIG. 2, twisting battery cover 4 relative to vibrating body 3 and about the axis A-A unfastens the battery cover from the vibrating body, and button-type batteries 11 are loaded into or unloaded from the battery chamber of the vibrating body. A plurality of protrusions 3*a* on the outer surface of the distal end of vibrating body 3, and a plurality of protrusions 4*a* on the surface of battery cover 4 provide an anti-slip gripping means. Various arrangements of protrusions, grooves or ribs are possible, and other gripping surfaces such as checking and surface roughening or regular or irregular surface treatments such as knurling or cross-hatching are among possible alternatives to enhance gripping of cover 4.

Figure 3:
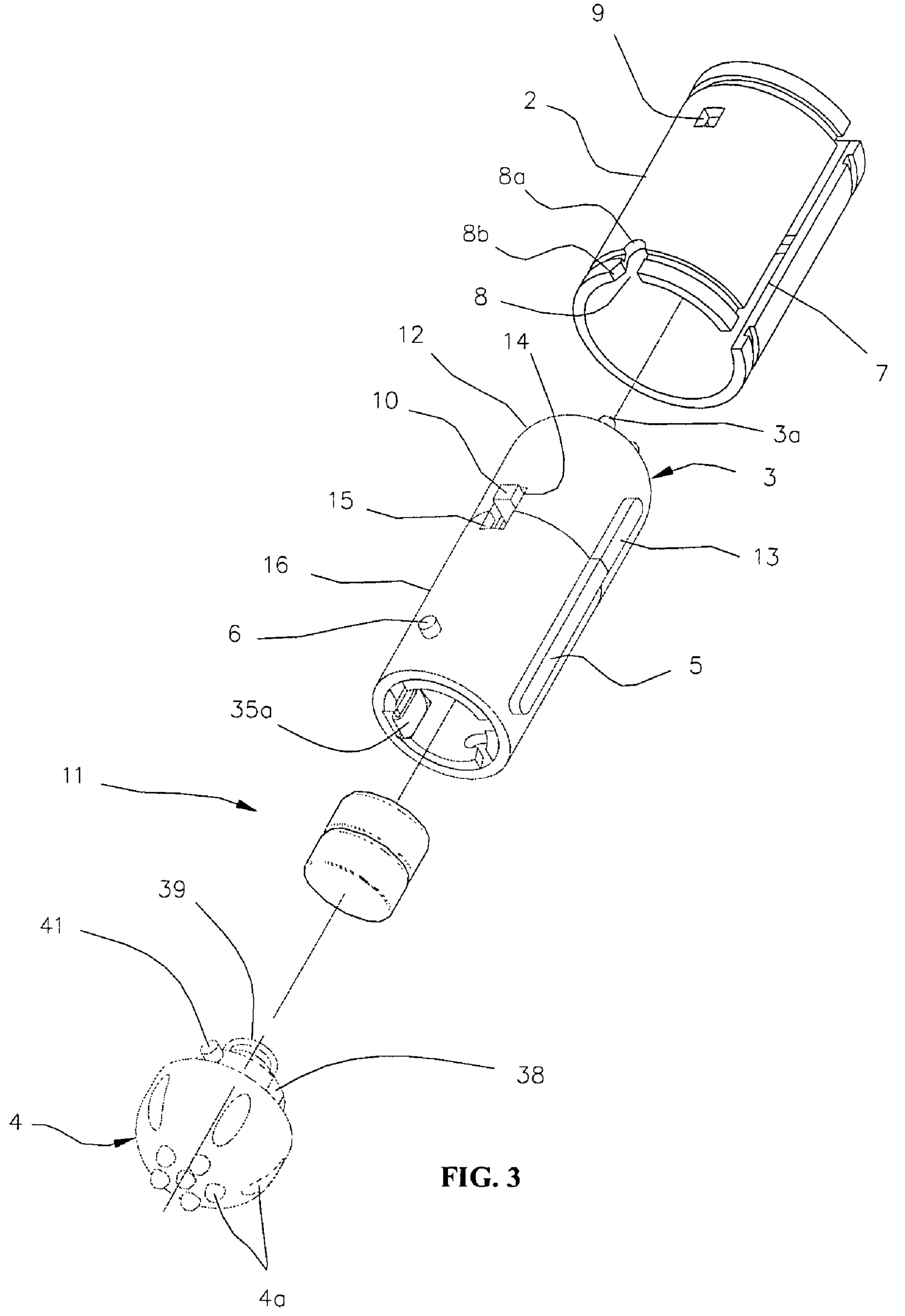
FIG. 3 illustrates a perspective-type view of the massage device shown in FIG. 2 with the outermost shell detached from the vibrating body in accordance with an embodiment of the presently described invention.

Referring to FIG. 3, an exploded or partly disassembled view, outmost shell 2 is shown detached from vibrating body 3, whereas the battery cover 4 is detached from the vibrating body as well.

Figure 4:
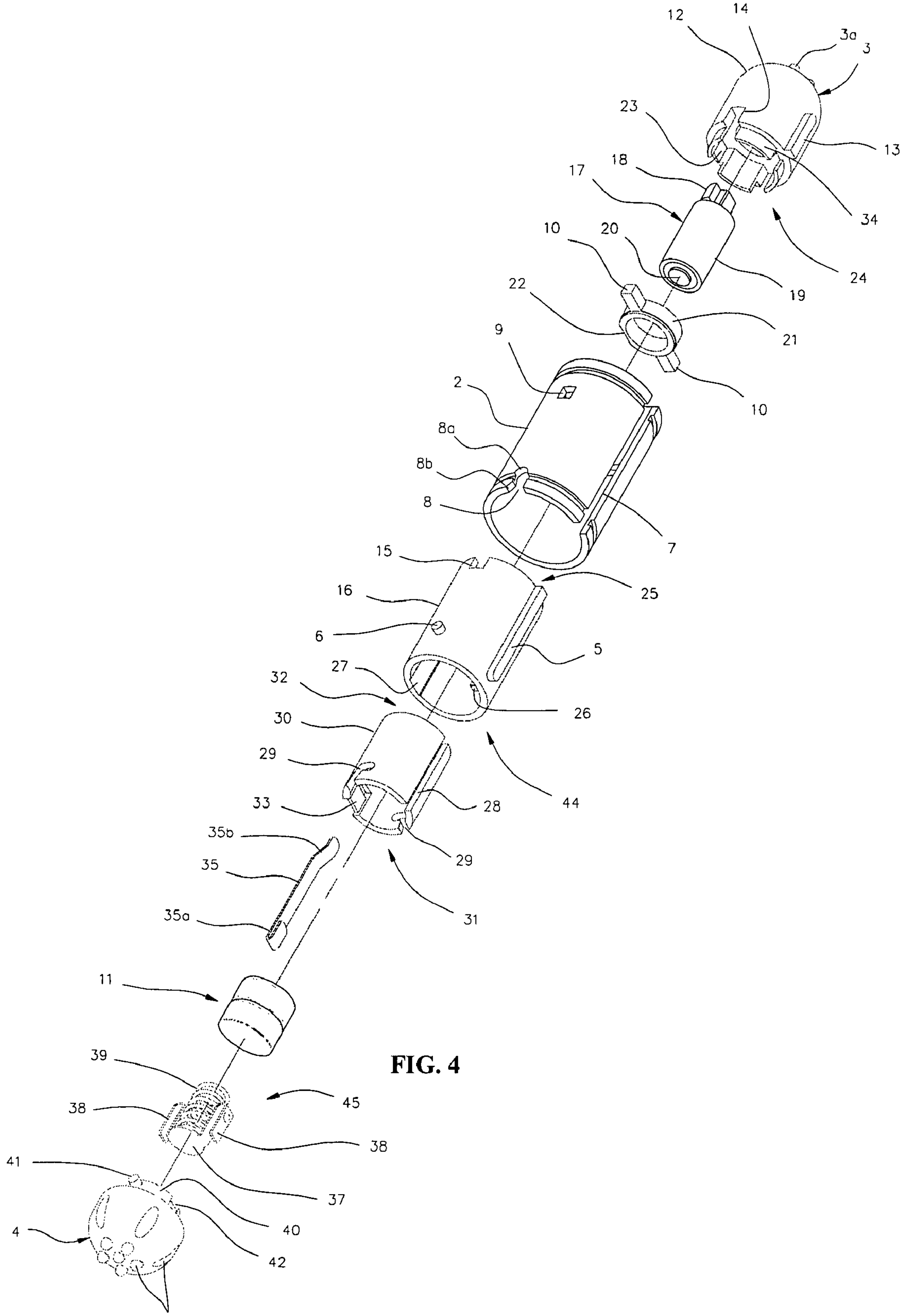
FIG. 4 illustrates an exploded view of the components making up the device of FIG. 1 in accordance with an embodiment of the presently described invention.

Referring to FIG. 4, showing still further disassembly, hollow casing 12 has one opening 24 at the proximal end for accommodating an electric motor 17, a plurality of protrusions 3*a* on the outer surface of the distal end, and a key portion 13 on the outer surface. At the edge of the opening end of the casing 12 there one or more slots 14 apart for accommodating one or more arms 10 of switch ring 21. For example, two slots 14 can be disposed circumferentially at 180° apart for accommodating one or more arms 10 of switch ring 21. At the edge of the opening end of the casing 12 there are circular shoulder segments 34 for engaging the hole of cylindrical casing 16 at its distal end 25. Further, at the edge of the opening end of the casing 12 and on the internal surface there is a recess 23 for accommodating contact blade or plate 35.

The vibration generator formed by electric motor 17 has an eccentric mass 18 fixed on its shaft, an electric pole 19 defined by the outer surface of the motor, and another electric pole 20 disposed at the end of the motor. Switch ring 21 has a center hole slideably engaged with the external diameter of electric motor 17, and an external flat face 22 for engaging with contact plate 35. On the edge of distal end 25 of cylindrical casing 16 there one or more slots 15 for accommodating one or more arms 10 of switch ring 21. For example, there can be two slots 15 disposed circumferentially at 180° apart for accommodating arms 10 of switch ring 21. On the outer surface of the casing 16 is key portion 5. On the outer surface of the casing 16 is cylindrical block 6 for engaging with slot 8 of outermost shell 2. On the internal surface of the casing 16 there is a longitudinal key portion 26 for engaging with slot 28 of inner sleeve 30, and on the other side of the internal surface there is a longitudinal recess 27 for accommodating contact plate 35. In an embodiment, slot 28 extends from a distal end 32 of sleeve 30 to a proximal end 31 of sleeve 30.

On the edge of the proximal end 31 of inner sleeve 30 there are two L-shape slots 29 disposed circumferentially at 180° apart for engaging with locking blocks 41 of battery cover 4 to lock the cover on to vibrating body 3. Also, at the proximal end 31 of inner sleeve 30 and on the internal surface there is a recess 33 for securing the fixing end 35*a* of contact plate 35. The inner sleeve 30 is inserted, from the opening 44, into the cylindrical casing 16 and fixed for providing the internal structural features. Contact spring assembly 45 is formed by a metallic blade or plate 37 with two locating tags 38 carrying a compression spring 39. Spring assembly 45 is fixed with its locating tags 38 seated in recesses 42 on distal end 40 of battery cover 4.

Figure 5:
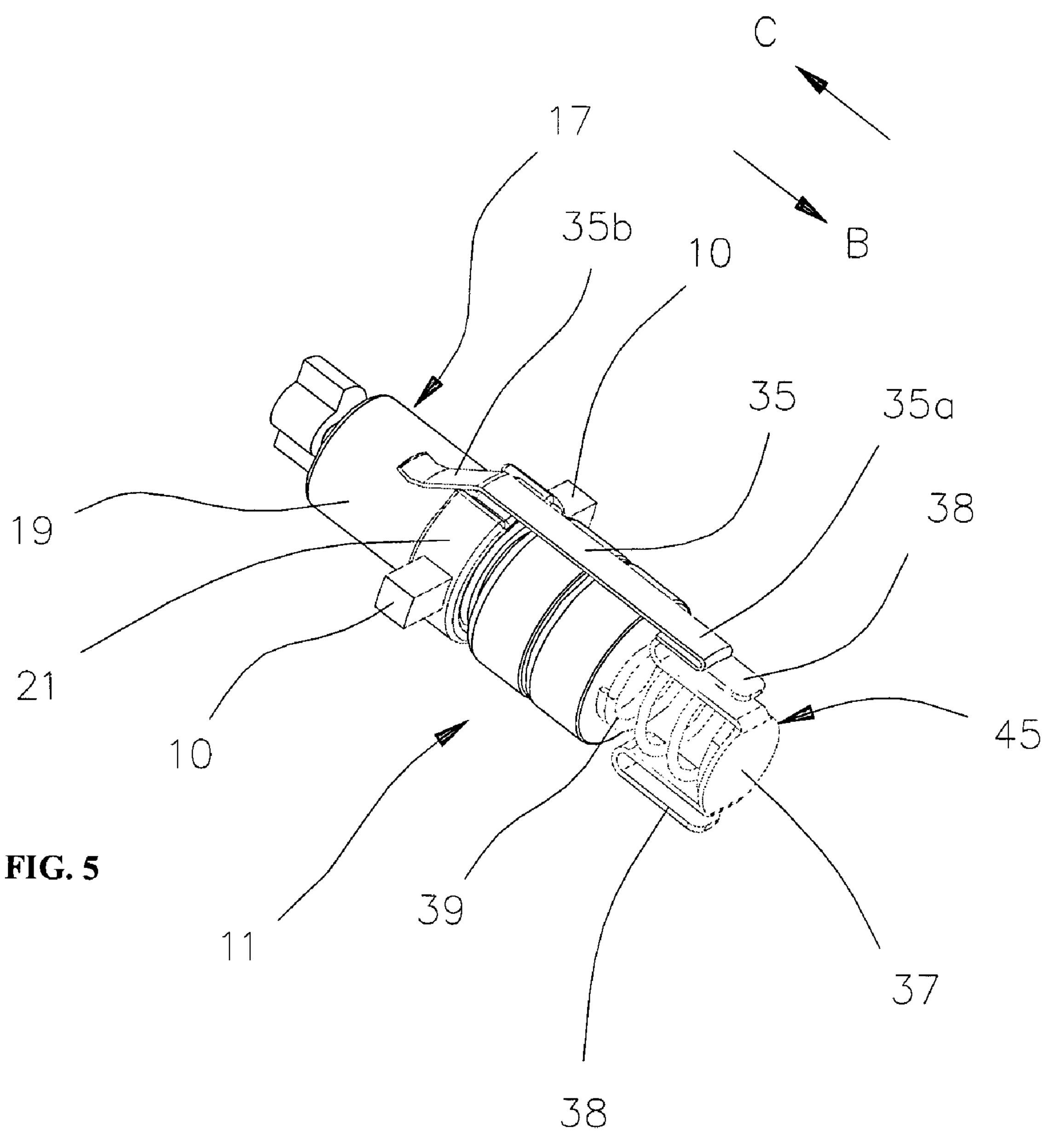
FIG. 5 illustrates a perspective-type view of the components forming the power switching mechanism in accordance with an embodiment of the presently described invention.

Referring to FIG. 5, when battery cover 4 is locked on vibrating body 3, spring assembly 45 is brought into effect to push battery set 11 toward electric motor 17, i.e., in the distal direction, and so enables the negative pole (not shown) of the first battery to contact pole 20 of the motor, and at the same time a tag 38 of the assembly 45 is connected to the fixing end 35*a* of the contact plate 35. When switch ring 21 is moved in the direction B, it is equivalent to moving the block 6 towards the slot position 8*a* (FIG. 1), so that contact plate 35 then will bias into contact with pole 19 of the motor to close the power circuit and so to provide the switch-on function. Conversely, when switch ring 21 is moved in the proximal direction by the sleeve in the direction C it is equivalent to moving block 6 towards slot position 8*b* (FIG. 1), so that the switch ring 21 will push portion 35*b* of contact plate 35 and move it away from pole 19 to open the power circuit and so to provide the switch-off function.

In view of the foregoing description of the present invention and possible variations of embodiments and methodology it will be seen that the several objects of the invention are achieved and other advantages are attained. As modifications could be made in the constructions and methodology herein described and illustrated without departing from the scope of the invention, all matter contained in the foregoing description or shown in the accompanying drawings shall be interpreted as illustrative rather than limiting.

What is claimed is:

1. A miniature electrically powered massage vibrator includes:

- a vibrating body including an outermost shell and a vibration generator;
- a battery power source capable of powering the vibration generator; and
- a power switching mechanism, wherein the shell is slideable relative to the vibrating body for providing an on/off switching function to the power switching mechanism, wherein the vibrating body includes a key extending longitudinally along the vibration body, the shell being prevented from rotating relative to the vibration body by the key.

2. The massage vibrator as set forth in claim 1 wherein the shell includes a longitudinal slot engaging the key, the longitudinal slot permitting the shell to slide in a longitudinal direction relative to the vibrating body between on and off positions.

3. The massage vibrator as set forth in claim 2 wherein the vibrating body comprises a rounded head carrying a plurality of protrusions on an outer surface of a distal end of the vibrating body for transfer of vibrations from the vibration generator.

4. The massage vibrator as set forth in claim 2 wherein the vibration generator is an electric motor having a shaft carrying an eccentric mass, the motor being proximate to the a distal end of the vibration generator.

5. The massage vibrator as set forth in claim 4 wherein the motor has two poles for being provided with electric power, the vibrating body including a battery set located within the shell, the battery set providing a first pole proximate the motor for contacting a corresponding first pole of the motor and a second pole remote from the motor, and a contact blade for presenting a second pole of the battery for providing a connection for a corresponding second pole of the motor, the battery set being positioned in stacked relation rearward of the motor, a sleeve being slideable between on and off positions, the on position being provided by the sleeve being moved forward toward the distal end of the vibrating body for urging the battery set toward the motor to bring the first pole of the battery set into contact with the first pole of the motor for completing an electric circuit for producing a motor-on function, and the sleeve being slideable rearward toward a proximal end of the vibrating body for opening the electric circuit for producing a motor-off function, being thereby the off position of the sleeve.

6. The massage vibrator as set forth in claim 5 wherein the vibrating body comprises a rounded head having an outer surface of the distal end of the vibrating body for transfer of vibrations from the vibration generator.

7. The massage vibrator as set forth in claim 6 further comprising a switch ring distal to the battery set, and coaxial with the battery set, the switch ring being shiftable longitudinally in response to axial movement of the sleeve distally and proximally.

8. The massage vibrator as set forth in claim 7 wherein the switch ring is enclosed by the sleeve and is engaged at opposite sides to the sleeve, the switch ring when moved distally by the sleeve permitting the contact blade to move into a position for completing a circuit between the battery set and the motor, and when moved proximally by the sleeve causing the contact blade to move into a position to open said circuit.

* * * * *

UNITED STATES PATENT AND TRADEMARK OFFICE

CERTIFICATE OF CORRECTION

PATENT NO. : 7,871,386 B2
APPLICATION NO. : 11/724819
DATED : January 18, 2011
INVENTOR(S) : Simon Siu Man Nan It is certified that error appears in the above-identified patent and that said Letters Patent is hereby corrected as shown below:

Column 2, line 52: "mechanism" should read --mechanism.--

Column 3, line 53: "there one" should read --there are one--

Column 4, line 64 (Claim 4, line 3): "to the a" should read --to a--

Signed and Sealed this
Thirty-first Day of July, 2012

David J. Kappos

David J. Kappos
*Director of the United States Patent and Trademark Office*